United States Patent [19]

Stenzel

[11] 4,434,167
[45] Feb. 28, 1984

[54] PYRIMIDYL THIOUREAS USEFUL FOR THE TREATMENT OF HYPERTENSION AND HYPERLIPIDEMIA

[75] Inventor: Wolfgang Stenzel, Reinbek, Fed. Rep. of Germany

[73] Assignee: Beiersdorf aktiengesellschaft, Fed. Rep. of Germany

[21] Appl. No.: 257,444

[22] Filed: Apr. 24, 1981

Related U.S. Application Data

[62] Division of Ser. No. 92,134, Nov. 7, 1979.

[51] Int. Cl.³ .......................................... A61K 31/505
[52] U.S. Cl. .................................. 424/251; 544/311; 544/327; 544/316; 544/326; 544/299
[58] Field of Search ................ 424/251; 544/327, 299, 544/316, 317, 311, 326

[56] References Cited

U.S. PATENT DOCUMENTS

| | | | |
|---|---|---|---|
| 3,755,326 | 8/1977 | Berger et al. | 424/251 |
| 3,759,921 | 9/1973 | Paget | 424/251 |
| 3,818,033 | 6/1974 | Hayes et al. | 544/333 |
| 3,920,655 | 11/1975 | Rufer et al. | 544/333 |
| 4,108,982 | 8/1978 | Amschler | 424/272 |
| 4,308,272 | 12/1981 | Wierenga et al. | 424/251 |

FOREIGN PATENT DOCUMENTS

| | | |
|---|---|---|
| 2068499 | 8/1971 | France . |
| 1267433 | 3/1972 | United Kingdom . |

OTHER PUBLICATIONS

Chem Abstracts, vol. 72, 31191d, (1970).
Weygand-Hilgetag, Organisch Chemische Experimentierkunst, 4th Edition, Joh Amb. Barth, Leipzig, (1970), 515-516.
B. Helwig, *Machine Arznamittel*, 4th Edition (1977), 926-928.
Hackh's Chemical Dictionary, p. 16, Fourth Edition, (1969), McGraw-Hill, N.Y.

*Primary Examiner*—Nicholas S. Rizzo
*Attorney, Agent, or Firm*—Jordan B. Bierman; Linda Bierman

[57] ABSTRACT

Pyrimidyl thioureas of the formula

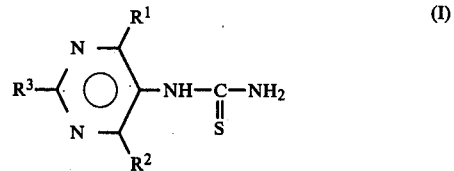

wherein $R^1$, $R^2$, and $R^3$ individually represent hydrogen, halogen, a linear or branched alkoxy group, or a linear or branched alkyl group, said groups having 1 to 8 carbon atoms, and their pharmaceutically acceptable salts. These compounds are useful for the treatment of hyperlipidemia and hypertension.

Compositions containing these compounds as well as methods of use and preparation thereof are also disclosed.

11 Claims, No Drawings

PYRIMIDYL THIOUREAS USEFUL FOR THE TREATMENT OF HYPERTENSION AND HYPERLIPIDEMIA

The present application is division of Ser. No. 92,134, filed Nov. 7, 1979, which claims the priority of German Application Nos. P 28 49 537.6 of Nov. 15, 1978 and P 29 37 023.8 of Sept. 9, 1979; and the present application also claims the priority of German Application No. P 30 16 767.0 filed Apr. 30, 1980.

The present application is directed to certain thioureas, their use as pharmaceuticals, and methods of preparation thereof. More specifically, it has been found that certain compounds falling within the foregoing class possess excellent hypolipidemic and hypotensive characteristics.

The compounds of the present invention are represented by the formula

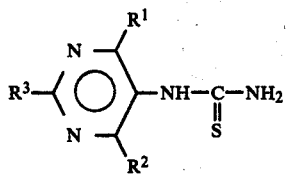

wherein $R^1$, $R^2$, and $R^3$ are individually hydrogen, halogen, linear or branched alkoxy groups, or linear or branched alkyl groups. The alkoxy and alkyl groups, in the broadest scope of the invention, have 1 to 8 carbon atoms. In a more preferred form of the invention, each of these groups contains 1 to 4 carbon atoms. Pharmaceutically acceptable salts of these basic compounds are also suitable.

Preferred are compounds of formula I, wherein $R^1$, $R^2$ and $R^3$ are alkoxy groups and/or alkyl groups. Especially preferred alkoxy groups are methoxy groups and ethoxy groups, especially methoxy groups. Especially preferred alkyl groups are methyl groups and ethyl groups, especially methyl groups. Preferably two of the substituents are alkoxy groups and the third substituent is hydrogen or an alkoxy group.

It has been found that the cholesterol lowering and triglyceride reducing effects in hyperlipidemic mice can be achieved in a dosage range of 1 to 300 mg/kg of body weight. It has been found that the new compounds possess both stronger hypolipidemic effects and reduced toxicity, especially when compared with such known drugs as clofibrate. This is particularly true for those compounds wherein $R^1$ and $R^2$ are alkoxy and $R^3$ is hydrogen.

In addition to the foregoing, these compounds exhibit valuable anti-hypertensive properties. In hypertensive rats, a dose of 1 to 30 mg/kg produced these therapeutic effects and no central side effects. Similarly, the alpha-receptor blockade, which is undesirable because of annoying accompanying effects, was also absent. Hence, the compounds of the present invention are suitable for humans for the treatment of hyperlipidemia and/or diseases of the cardiac-circulatory system, especially hypertension. The daily dose is between 10 and 1000 mg/person and it is preferably given two to four times a day in amounts of 5 to 500 mg/person. Alternatively, it can be given with advantage once a day in a time-release form. The preferred daily dose is from 50 to 300 mg per person.

By a suitable selection of $R^1$, $R^2$, and $R^3$, the therapeutic effect can be influenced so that either the hypolipidemic or hypotensive property predominates. The following are examples of compounds according to the present invention which exhibit the desirable therapeutic effects:

N-(4,6-dimethoxy-5-pyrimidyl)-thiourea
N-(4-ethoxy-6-methoxy-5-pyrimidyl)-thiourea
N-(4-isopropoxy-6-methoxy-5-pyrimidyl)-thiourea
N-(4-butoxy-6-methoxy-5-pyrimidyl)-thiourea
N-(4,6-diethoxy-5-pyrimidyl)-thiourea
N-(4,6-dibutoxy-5-pyrimidyl)-thiourea
N-(4-methoxy-6-methyl-5-pyrimidyl)-thiourea
N-(4,6-dimethyl-5-pyrimidyl)-thiourea
N-(2,4-dimethoxy-5-pyrimidyl)-thiourea
N-(2-chloro-4-methyl-5-pyrimidyl)-thiourea
N-(2-ethoxy-4-methoxy-5-pyrimidyl)-thiourea
N-(2,4-diethoxy-5-pyrimidyl)-thiourea
N-(2,4-diisopropoxy-5-pyrimidyl)-thiourea
N-(4-methoxy-2-methyl-5-pyrimidyl)-thiourea
N-(2-methyl-4-propoxy-5-pyrimidyl)-thiourea
N-(2-methyl-5-pyrimidyl)-thiourea
N-(2-isopropyl-5-pyrimidyl)-thiourea
N-(4-methyl-5-pyrimidyl)-thiourea
N-(4-ethyl-5-pyrimidyl)-thiourea
N-(4-butyl-5-pyrimidyl)-thiourea
N-(2-methoxy-5-pyrimidyl)-thiourea
N-(4-methoxy-5-pyrimidyl)-thiourea
N-(4-ethoxy-5-pyrimidyl)-thiourea
N-(4-propoxy-5-pyrimidyl)-thiourea
N-(4-isopropoxy-5-pyrimidyl)-thiourea
N-(4-butoxy-5-pyrimidyl)-thiourea
N-(5-pyrimidyl)-thiourea
N-(2,4,6-trimethoxy-5-pyrimidyl)-thiourea
N-(2,4,6-trimethyl-5-pyrimidyl)-thiourea
N-(2,4-dimethoxy-6-methyl-5-pyrimidyl)-thiourea
N-(2,4-diethoxy-6-methyl-5-pyrimidyl)-thiourea
N-(4,6-dimethoxy-2-methyl-5-pyrimidyl)-thiourea
N-(4,6-dimethoxy-2-isopropyl-5-pyrimidyl)-thiourea
N-(4-ethoxy-6-methoxy-2-methyl-5-pyrimidyl)-thiourea
N-(4-ethoxy-2-ethyl-6-methoxy-5-pyrimidyl)-thiourea
N-(2-butyl-4-methoxy-6-propoxy-5-pyrimidyl)-thiourea
N-(2-chloro-4-methyl-6-methoxy-5-pyrimidyl)-thiourea
N-(2-chloro-4-propyl-6-isopropoxy-5-pyrimidyl)-thiourea
N-(4-chloro-6-methoxy-2-methyl-5-pyrimidyl)-thiourea
N-(4-chloro-6-ethoxy-2-isopropyl-5-pyrimidyl)-thiourea
N-(4-methoxy-6-pentyloxy-5-pyrimidyl)-thiourea
N-(4-methoxy-2-t.-pentyl-5-pyrimidyl)-thiourea
N-(2-methoxy-4-pentyloxy-5-pyrimidyl)-thiourea
N-(4,6-dihexyloxy-5-pyrimidyl)-thiourea
N-(2-heptyl-4-methoxy-5-pyrimidyl)-thiourea
N-(4-heptyloxy-2-pentyl-5-pyrimidyl)-thiourea
N-(2-chloro-4-methyl-6-octyloxy-5-pyrimidyl)-thiourea
N-(2-octyl-4-methyl-6-heptoxy-5-pyrimidyl)-thiourea
N-(2-bromo-4-methyl-6-methoxy-5-pyrimidyl)-thiourea Especially suitable compounds are N-(4,6-dimethoxy-5-pyrimidyl)-thiourea; N-(2,4-dimethoxy-5-pyrimidyl)-thiourea; N-(4,6-dimethoxy-2-methyl-5-pyrimidyl)-thiourea, and N-(4,6-diethoxy-5-pyrimidyl)-thiourea. These compounds exhibit both desirable effects.

The use of the usual derivatives, as well as suitable diluents, adjuvants, or vehicles is also contemplated. Administration can be oral or parenteral. The compounds can take the form of tablets, pills, syrups, suspensions, and liquids for oral adminstration. When administered parenterally, they should be provided as solutions or suspensions.

The tablets may contain additives, adjuvants, granulating agents, aids to disintegration, binders, lubricants, etc. The nature of these materials is generally known and need not be expressly set forth here.

The tablets can also be coated in order to delay disintegration and absorption in the gastro-intestinal tract. In this manner, the effectiveness of the active ingredient can be extended over a long period of time. The pharmaceutical preparations can advantageously contain the active ingredient in an amount of 0.1 to 90%, preferably 1.0 to 90%. The balance being usually a vehicle or adjuvant. For ease of manufacture and administration, the solid forms (such as tablets and capsules) are preferred. Such preparations can contain the active substance in an amount of 50 to 300 mg, corresponding to the preferred daily dose.

The compounds of the present invention can be prepared from aminopyrimidines of the formula

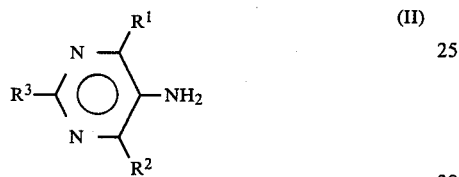

by reaction with benzoylisothiocyanate, whereby the corresponding benzoylthioureas are obtained which are then hydrolized to produce the desired compound. The benzoylisothiocyanate can be obtained from ammonium thiocyanate and benzoyl chloride.

In a preferred method of preparing the compounds of the present invention, the ammonium thiocyanate, benzoyl chloride, and aminopyrimidine are reacted together in an organic solvent under heating. The solvent is preferably boiling acetone. It is preferred to carry out the reaction from ambient temperature to the boiling point of the solvent over a period of 30 minutes to 3 hours, preferably 30 minutes to 1 hour. The reaction mixture is then introduced into water and the reaction product is extracted with a solvent which is immiscible with water, preferably chloroform. The thiourea derivatives obtained are then hydrolized, e.g. in the presence of bases and, if necessary, with heating in order to separate the benzoyl radical. Suitable bases are dilute lye and sodium methylate solution.

The aminopyrimidines used as starting materials are either known or obtainable in a known manner from available starting materials (see D. J. Brown, "The Pyrimidines", 1962 Interscience Publishers).

In the thioureas of the present invention wherein $R^1$ and $R^2$ are alkoxy (preferably methoxy), and $R^3$ has the usual meaning, a new alkoxy radical can be introduced by reacting with a corresponding alcoholate. This reaction is preferably carried out with equimolar amounts of sodium alcoholate in an alcohol which corresponds to the alcoholate. It is desirable to carry out the reaction at an elevated temperature, preferably at the boiling temperature of the alcohol. In this manner the compounds of the present invention wherein $R^1$ and $R^2$ are alkoxy radicals which may be different from each other can be formed.

Alkoxypyrimidines can be obtained from halopyrimidines by reaction with alcoholate in a suitable solvent. It is preferred that the solvent be an alcohol corresponding to the alcoholate. If a plurality of halogen atoms is present on the nucleus, either one or more can be substituted by the corresponding alkoxy groups by a suitable selection of reaction conditions, particularly the concentration of alcoholate and reaction temperature. The process is most suitable for those compounds wherein the halogen is chlorine. It is also possible to introduce different alkoxy groups successively and the reactions can generally be carried out with both the halo-5-nitropyrimidines and with halo-5-aminopyrimidines.

The chlorine atoms which are linked to the pyrimidine ring can be separated by catalytic hydration in the presence of a base. The removal of such atoms can also be effected by reacting corresponding chloropyrimidines with hydrazine, followed by separation of the hydrazine group with silver (I) oxide. The hydrazine reaction is preferably carried out in a suitable solvent (especially methanol or ethanol), at temperatures between 0° C. and the boiling point of the solvent. The reaction with silver (I) oxide is also carried out under the same general conditions.

Chloronitropyrimidines of the formula

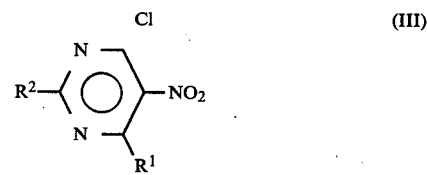

can be obtained from hydroxypyrimidines of the formula

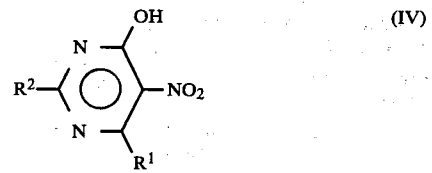

wherein $R^1$ and $R^2$ are hydrogen, halogen, hydroxy, or alkyl or alkoxy groups with 1 to 8 carbon atoms each, by reaction with a suitable chlorinating agent. The most preferred process uses phosphoroxy trichloride in the presence of a tertiary amine, such as diethylene aniline. These reactions are most preferably carried out without solvents at an elevated temperature.

The substituted nitropyrimidines can be converted to the aminopyrimidines of Formula II by catalytic hydration in the presence of Raney nickel at a pressure of 1 to 10 bar. Alcohols can be used as the solvent, and methanol is preferable. The reaction temperature is from room temperature to approximately 50° C.

The following examples are intended to illustrate the preparation of compounds according to the present invention.

PREPARATION EXAMPLE 1

N-(4,6-dimethoxy-5-pyrimidyl)-thiourea (a) 200 g 4,6-dihydroxypyrimidine are introduced at 15° to 20° C. into a mixture of 720 ml glacial acetic acid and 230 ml nitric acid (96%). The mixture is stirred for 30 minutes, after which it is poured over ice. The precipitate formed is removed, washed with ice water, and subsequently dried at 80° C. Yield: 254 g 4,6-dihydroxy-5-nitropyrimidine. M.P. >300° C.

(b) 135 g of the product of (a) are stirred into 440 ml phosphoroxy-trichloride. Then 160 ml N,N-diethylaniline are added slowly over a period of 1 hour at 120° C. Subsequently, the excess phosphoroxy-trichloride is distilled off, the residue is poured over ice, and the precipitate obtained is filtered off. The precipitate is taken up in some water and stirred, after which it is neutralized with sodium bicarbonate. The residue is filtered off and it is boiled with 500 ml cyclohexane. The clear solution obtained is poured off from the undissolved residue to isolate the reaction product, and evaporated. After drying, 131 g 4,6-dichloro-5-nitropyrimidine are obtained. M.P. 103° C.

(c) Into a solution of 62 g NaOH in 1200 ml methanol are introduced 120 g of the product of (b). After heating under reflux for 1 hour, the reaction product is cooled and placed in 3 liters of water. The crystals obtained are filtered off and dried. 87 g 4,6-dimethoxy-5-nitropyrimidine having a melting point of 168° to 170° C. is obtained.

(d) 125 g of the product of (c) are dissolved in 1.5 liters ethanol and hydrated in a refined steel autoclave for 5 hours in the presence of 40 g Raney nickel at 2.5 bar. The catalyst is filtered off and the filtrate concentrated. 88 g 5-amino-4,6-dimethoxy-pyrimidine are obtained. M.P. 94° to 96° C.

(e) To a solution of 12.9 g ammonium thiocyanate in 120 ml anhydrous acetone are added slowly in drops 25.3 g benzoyl chloride. The mixture is heated for 5 minutes under reflux, and 27 g 5-amino-4,6-dimethoxy-pyrimidine, dissolved in 50 ml acetone, are added in drops. The boiling is continued for another hour under reflux. The mixture is then cooled and placed in 1.5 liters water. Subsequently, it is extracted with chloroform, and dried over magnesium sulfate. After distilling off the chloroform, the residue is triturated with ether and vacuum treated. Yield: 34 g (61%) N-benzoyl-N'-(4,6-dimethoxy-5-pyrimidyl)-thiourea. M.P. 193° C.

(f) 34 g of the N-benzoyl thiourea derivative thus obtained are boiled for 5 minutes in 30 ml of 10% NaOH. After cooling, the mixture is acidified with concentrated HCl and adjusted to a pH of 9 with 15% aqueous ammonia solution. The precipitated crystals are vacuum treated and washed with water. 16 g (70%) N-(4,6-dimethoxy-5-pyrimidyl)-thiourea are obtained. M.P. 214° C.

PREPARATION EXAMPLE 2

N-(4-methoxy-5-pyrimidyl)-thiourea (a) 100 g 5-nitro 4,6-dichloropyrimidine are heated in 1000 ml sodium ethylate solution (16.8 g sodium) for 10 hours to 50° C. Then the reaction mixture is evaporated under vacuum and the residue is stirred with water and vacuum treated. Subsequently, it is extracted several times with hot petroleum ether (boiling range 40° to 60° C.). After cooling, the crystals are vacuum treated and dried. 46 g 4-chloro-6-methoxy-5-nitropyrimidine are obtained having a melting point of 65° C.

(b) 15 g 4-chloro-6-methoxy-5-nitropyrimidine are dissolved in 600 ml ethanol. Then 8.1 ml hydrazine hydrate in 150 ml ethanol are added in drops at −8° C. After one hour the crystals obtained are vacuum treated and dried. Yield: 14.5 g 4-hydrazino-6-methoxy-5-nitropyrimidine, M.P. 155° C.

(c) 14 g 4-hydrazino-6-methoxy-5-nitropyrimidine are dissolved in 3.6 liters of methanol and stirred for 10 hours at 40° C. with 61.9 g of freshly prepared silver (I) oxide. Then the mixture is filtered and the solution evaporated. 10.5 g 4-methoxy-5-nitropyrimidine with a melting point of 193° to 195° C. is obtained.

(d) 10 g 4-methoxy-5-nitropyrimidine in 500 ml methanol are hydrated for 2.5 hours at 2 bar in the presence of 4.5 g Raney nickel. After filtration, the solution is concentrated. 8.0 g 5-amino-4-methoxypyrimidine having a melting point of 71° to 74° C. are obtained.

(e) Similar to Example 1, N-benzoyl-N'-(4-methoxy-5-pyrimidyl)-thiourea is prepared from 5-amino-4-methoxypyrimidine.

(f) 6.0 g N-benzoyl-N'-(4-methoxy-5-pyrimidyl)-thiourea are dissolved in 120 ml sodium ethylate solution (0.8 g sodium). After 1 hour, the solution is neutralized with diluted hydrochloric acid. The mixture is concentrated and the residue is washed with water and recrystallized from a methanol/water mixture. 2.3 g N-(4-methoxy-5-pyrimidyl)-thiourea having a melting point of 182° to 183° C. (decomp.) are obtained.

PREPARATION EXAMPLE 3

N-(4-ethoxy-6-methoxy-5-pyrimidyl)-thiourea 3.0 g N-(4,6-dimethoxy-5-pyrimidyl)-thiourea are mixed with a sodium-ethylate solution (0.317 g sodium in 30 ml absolute ethanol) and heated for 3 hours under reflux. After cooling the mixture is neutralized. The reaction product is vacuum treated and purified chromatographically on silica gel (developer; chloroform/methanol 95:5). 0.6 g N-(4-ethoxy-6-methoxy-5-pyrimidyl)-thiourea having a melting point of 186° to 187° C. are obtained.

The compounds listed in the following table were synthetized in analogy to the foregoing preparation examples.

| Preparation Example | R1 | R2 | R3 | Mp. deg. C. |
|---|---|---|---|---|
| 5 | OC$_2$H$_5$ | OC$_2$H$_5$ | H | 242 |
| 6 | OC$_4$H$_9$ | OC$_4$H$_9$ | H | 105–106 (hydrate) |
| 7 | OCH$_3$ | CH$_3$ | CH$_3$ | 212 |
| 8 | OCH$_3$ | OCH$_3$ | CH$_3$ | 228 |
| 9 | OCH$_3$ | H | OCH$_3$ | 173 |
| 10 | CH$_3$ | OCH$_3$ | Cl | 186 (decomp.) |
| 11 | OCH$_3$ | Cl | CH$_3$ | from 190 (decomp.) |

The production of pharmaceuticals using compounds of the present invention is illustrated by the following examples.

EXAMPLE 1

Production of Tablets and Capsules

Tablets and capsules which contain the components indicated below are produced according to known methods. They are suitable for the treatment of hyperlipidemia in doses of one tablet or capsule two to four times daily.

| Components | Weight (mg) Tablet | Capsule |
|---|---|---|
| N—(4,6-dimethoxy-5-pyrimidyl)-thiourea | 100 | 100 |
| Tragacanth | 10 | — |
| Lactose | 247.5 | 300 |
| Corn Starch | 25 | — |
| Talcum | 15 | — |
| Magnesium stearate | 2.5 | — |

| Components | Weight (mg) Tablet | Capsule |
|---|---|---|
| | 400 | 400 |

EXAMPLE 2

The lipid-reducing action of N-(4,6-dimethoxy-5-pyrimidyl)-thiourea is tested on hyperlipidemic mice in analogy to a testing method indicated in "Screening Methods in Pharmacology", Robert A. Turner, 1965, Academic Press, New York and London; and Garattine et al, Arzneimittelforschung 9,206, (1959). The compound is administered perorally at a dosage level of 10 mg/kg. The cholesterol level is reduced by 25%, and the triglyceride level by 27%.

EXAMPLE 3

The antilipidemic and antihypertensive action of N-(2,4-dimethoxy-5-pyrimidyl)-thiourea is tested on hyperlipidemic mice and spontaneously hypertensive rats.

The mice are given a dose of 100 mg/kg perorally, and a reduction of the cholesterol level by 38% and of the triglyceride level by 49% is achieved.

The rats are given a dose of 30 mg/kg perorally and the blood pressure is reduced by 30%.

EXAMPLE 4

The antihypertensive action of N-(4,6-dimethoxy-2-methyl-5-pyrimidyl)-thiourea is tested on spontaneously hypertensive rats. The compound is administered perorally in a dose of 30 mg/kg. The blood pressure is reduced by 30%.

Although only a limited number of specific embodiments of this invention have been expressly disclosed, it is, nonetheless, to be broadly construed and not to be limited except by the character of the claims appended hereto.

EXAMPLE 5

Production of Tablets and Capsules

Tablets and capsules which contain the components indicated below are produced according to known methods. They are suitable for the treatment of hypertension in doses of one tablet or capsule two to four times daily.

| Components | Weight (mg) Tablet | Capsule |
|---|---|---|
| N—(2,4-dimethoxy-5-pyrimidyl)-thiourea | 50 | 50 |
| Tragacanth | 10 | — |
| Lactose | 297.5 | 350 |
| Corn Starch | 25 | — |
| Talcum | 15 | — |
| Magnesium stearate | 2.5 | — |

| Components | Weight (mg) Tablet | Capsule |
|---|---|---|
| | 400 | 400 |

I claim:

1. A composition for the treatment of hypertension and/or hyperlipidemia comprising an amount of a compound of the formula

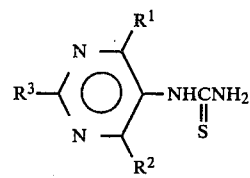

wherein $R^1$, $R^2$, and $R^3$ are individually hydrogen, halogen, linear or branched alkoxy, or linear or branched alkyl, said alkoxy and said alkyl having 1 to 8 carbon atoms each, or pharmaceutically acceptable salts thereof; which is sufficient, when administered to a warm blooded animal, to provide a hypotensive and/or hypolipid effect in said animal, and a pharmaceutically acceptable carrier.

2. A method for treating hyperlipidemia and/or hypertension comprising administering to a warm blooded animal an effective amount of a compound of the formula

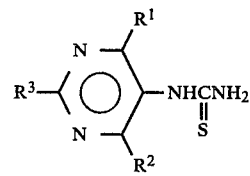

wherein $R^1$, $R^2$, and $R^3$ are individually hydrogen, halogen, linear or branched alkoxy, or linear or branched alkyl, said alkoxy and said alkyl having 1 to 8 carbon atoms each, or pharmaceutically acceptable salts thereof.

3. The method of claim 2 for treating hypertension wherein said amount is from 10 to 1000 mg/day/person.

4. The method of claim 3 wherein said amount is from 50 to 300 mg/day/person.

5. The method of claim 3 wherein said compound is administered two to four times per day.

6. The method of claim 3 wherein said compound is administered once each day in time release form.

7. The composition of claim 1 wherein said alkoxy and alkyl groups each contain 1 to 4 carbon atoms.

8. The method for treating hyperlipidemia of claim 2 wherein said amount is 10 to 1000 mg/day/person.

9. The method of claim 8 wherein said amount is from 50 to 300 mg/day/person.

10. The method of claim 8 wherein said compound is administered two to four times per day.

11. The method of claim 8 wherein said compound is administered once each day in time release form.

* * * * *